United States Patent [19]

Martin

[11] Patent Number: 5,797,395
[45] Date of Patent: Aug. 25, 1998

[54] CONTINUOUS CARDIAC OUTPUT DERIVED FROM ARTERIAL PRESSURE WAVEFORM USING PATTERN RECOGNITION

[75] Inventor: James F. Martin, Carmel, Ind.

[73] Assignee: Eli Lilly and Company, Indianapolis, Ind.

[21] Appl. No.: 362,204

[22] Filed: Dec. 22, 1994

Related U.S. Application Data

[62] Division of Ser. No. 72,038, Jun. 3, 1993, Pat. No. 5,390,679.

[51] Int. Cl.[6] .................................................. A61B 5/215
[52] U.S. Cl. ............................ 128/673; 128/668; 128/713
[58] Field of Search .......................... 128/668, 672–683, 128/691, 692, 694, 713

[56] References Cited

U.S. PATENT DOCUMENTS

| | | | |
|---|---|---|---|
| 4,423,733 | 1/1984 | Grassi et al. | 128/419 |
| 4,450,527 | 5/1984 | Sramek | 364/415 |
| 4,509,526 | 4/1985 | Barnes et al. | 128/663 |
| 4,542,748 | 9/1985 | Roy | 128/713 |
| 4,572,206 | 2/1986 | Geddes et al. | 128/692 |
| 4,671,295 | 6/1987 | Abrams et al. | 128/663 |
| 4,674,518 | 6/1987 | Salo | 128/695 |
| 4,685,470 | 8/1987 | Sekii et al. | 128/692 |
| 4,722,347 | 2/1988 | Abrams et al. | 128/663 |
| 4,733,669 | 3/1988 | Segal | 128/663 |
| 4,807,638 | 2/1989 | Sramek | 128/672 |
| 4,819,655 | 4/1989 | Webler | 128/713 |
| 4,840,182 | 6/1989 | Carlson | 128/694 |
| 4,841,981 | 6/1989 | Tanabe et al. | 128/692 |
| 4,856,529 | 8/1989 | Segal | 128/661.08 |
| 4,858,614 | 8/1989 | Stevens et al. | 128/661.07 |
| 4,873,989 | 10/1989 | Einzig | 128/692 |
| 4,886,059 | 12/1989 | Weber | 128/207.15 |
| 4,898,176 | 2/1990 | Petre | 128/642 |
| 4,913,642 | 4/1990 | Weber | 425/275 |
| 4,914,604 | 4/1990 | Castelaz | 364/517 |
| 4,920,506 | 4/1990 | Castelaz | 364/602 |
| 4,926,875 | 5/1990 | Rabinovitz et al. | 128/691 |
| 4,930,099 | 5/1990 | Castelaz | 364/820 |
| 4,934,374 | 6/1990 | Ostlund et al. | 128/695 |
| 4,941,475 | 7/1990 | Williams et al. | 128/692 |

(List continued on next page.)

OTHER PUBLICATIONS

Kevin C. Ehlers et al., Ann.Biomed. Eng. 1986, pp. 219–239 "Cardiac Output Measurements. A Review of Current Techniques and Research".

Leonid B. Volfson, University of California, San Diego, pp. 1–172 "Pattern Recognition and Classification and Its Applications To Pre-Processing Arterial Pressure Waveform Signals and Image Processing Problems".

N. T. Kouchoukos, et al.; "Estimation of Stroke Volume in the Dog by a Pulse Contour Method"; May 1970; pp. 611–623 [Circulation Research, vol. XXVI].

Primary Examiner—Lee S. Cohen
Assistant Examiner—Bryan K. Yarnell
Attorney, Agent, or Firm—Fulwider Patton Lee & Utecht, LLP

[57] ABSTRACT

A system and method of determining cardiac output from a cardiac pressure waveform. The pressure waveform is continuously sensed and converted into a digital data stream. When a complete beat frame of data is sensed, the processor extracts a plurality of features from the sensed waveform which characterize the waveform. These features are compared to stored representative pressure waveforms (RPW's) which have a known cardiac output. The RPW's are obtained by applying a pattern recognition methodology to pressure waveforms of known cardiac output. In one embodiment the typical shapes function is used. The pattern recognition methodology results in classes and associated cardiac outputs which are stored as the RPW's. The features extracted from waveforms representative of unknown cardiac output are thus classified by the comparison to the RPW's. When a match is made between the extracted features and an RPW, the cardiac output of the selected RPW is output as the cardiac output of the patient.

28 Claims, 5 Drawing Sheets

U.S. PATENT DOCUMENTS

| | | | |
|---|---|---|---|
| 4,947,852 | 8/1990 | Nassi et al. | 128/662 |
| 4,947,854 | 8/1990 | Rabinovitz et al. | 128/662.04 |
| 4,949,724 | 8/1990 | Mahutte et al. | 128/713 |
| 4,951,682 | 8/1990 | Petre | 128/713 |
| 4,970,143 | 11/1990 | Guidoux et al. | 435/1 |
| 4,982,439 | 1/1991 | Castelaz | 382/42 |
| 5,001,631 | 3/1991 | Castelaz | 364/402 |
| 5,003,490 | 3/1991 | Castelaz et al. | 364/513 |
| 5,022,410 | 6/1991 | Hall et al. | 128/695 |
| 5,025,795 | 6/1991 | Kunig | 128/713 |
| 5,046,502 | 9/1991 | Junig | 128/670 |
| 5,046,505 | 9/1991 | Sekii et al. | 128/713 |
| 5,152,297 | 10/1992 | Meister et al. | 128/672 |
| 5,156,154 | 10/1992 | Valenta, Jr. et al. | 128/661.07 |
| 5,183,051 | 2/1993 | Kraidin et al. | 128/687 |
| 5,211,177 | 5/1993 | Chesney et al. | 128/672 |
| 5,241,964 | 9/1993 | McQuilkin | 128/672 |
| 5,251,626 | 10/1993 | Nickolls et al. | 607/14 |
| 5,265,615 | 11/1993 | Frank et al. | 128/672 |
| 5,265,617 | 11/1993 | Verrier et al. | 128/704 |
| 5,273,049 | 12/1993 | Steinhaus et al. | 128/696 |
| 5,285,796 | 2/1994 | Hughes | 128/668 |
| 5,316,004 | 5/1994 | Chesney et al. | 128/672 |
| B1 4,572,206 | 1/1991 | Geddes et al. | 128/692 |

CONTINUOUS CARDIAC OUTPUT DERIVED FROM ARTERIAL PRESSURE WAVEFORM USING PATTERN RECOGNITION

This is a division of application Ser. No. 08/072,038 filed Jun. 3, 1993, now U.S. Pat. No. 5,390,679.

BACKGROUND

The invention relates to cardiac output measurement, and more particularly, to a continuous cardiac output measuring system using pattern recognition.

Cardiac Output (CO) is used clinically to evaluate cardiac function in critically ill patients, aid in the diagnosis of cardiovascular disease, and guide therapeutic decisions in complex clinical situations. Continuous determinations of cardiac output are especially important for monitoring acutely ill patients, because their hemodynamic status may vary significantly during a short period of time. CO is defined as the volume of blood ejected by the left ventricle into the aorta per unit of time. Cardiac output is a function of the contractility of the ventricle, the afterload (i.e., the load the heart pumps against) and the preload (i.e. the volume of blood in the heart before it contracts). Cardiac output varies according to the body's needs for oxygen and nutrients. An average cardiac output for the population at large is 5.6 liters per minute. Another measure of heart output is cardiac index (CI), which is the cardiac output per square meter of body surface area. A normal human being of 70 kg. has a body surface area of about 1.7 square meters ($m^2$), giving a CI of about 3.0 liters/$m^2$ per minute. CI, like CO, varies with age. At 10 years of age CI is greater than 4 liters/$m^2$ per minute, while at the age of 80 CI declines to about 2.4 liters/$m^2$ per minute.

Prior systems have attempted to measure cardiac output both in a discrete and in a continuous manner. There are many desired features that a cardiac output measuring device should possess. For one, a cardiac output measuring device should have automated, continuous (in real-time) output measurements for the cardiac output. In addition, the cardiac output measurement device should have low invasiveness, present minimal risk to the patient, and not interfere with the desired hemodynamic measurement of the patient. Finally, the system should be relatively inexpensive to manufacture, easy to use in the clinical setting, accurate and compact.

A variety of cardiac output measurement devices are known in the art, all of which have certain disadvantages. One of the oldest techniques involves the Fick method, based on the theoretical principles described by Adolph Fick in 1870, that the total uptake or release of any substance by an organ is the product of blood flow to an organ and the arteriovenous concentration difference of the substance. One measurement technique consists of having the patient breathe pure $O_2$ from a spirometer with a $CO_2$ absorber, and measuring $O_2$ uptake directly from the net gas flux. Two catheters, one in the pulmonary artery and one in the brachial or femoral artery are used to sample mixed pulmonary artery and arterial blood to determine $O_2$ concentrations in the bloodstream. While the Fick method has the potential for high accuracy, most clinicians achieve actual accuracies in the range of 5% to 10%. Its disadvantages include: the patient's cardiac output and $O_2$ consumption must be constant over several minutes for accurate measurement; more than one catheter is required, which increases the risk of infection; a significant volume of blood is used by the test making it inconvenient for repeated cardiac output measurements, especially on infants or acutely ill patients; and, the monitors used to analyze gas concentrations are often bulky and these monitors are often not located near the patient, making real-time analysis difficult.

Another cardiac output measuring technique is the indicator dilution technique, which involves the injection of a predetermined amount of indicator dye into the right atrium, and measuring the dilution of the dye downstream. The average volume flow of blood flow is inversely proportional to the integrated area under the dilution curve. Besides using dye as an indicator, a saline solution can be used and the temperature and conductivity of the saline solution can be measured downstream for the same effect. The main disadvantage of indicator dilution techniques is recirculation of the indicator after the first measurement, which makes it difficult to make repeated measurements. For example, if indocyanine dye is used, only 50 of the dye is removed by the kidneys 10 minutes after injection. If saline is used as an indicator, repeated measurements can dilute the patient's blood supply. The use of catheters in this technique also increases the likelihood of infection, introduction of an air embolism or potential electrical hazard.

Other cardiac output measuring techniques that are invasive of the body include electromagnetic flow probe measurements from an electromagnetic flow probe surgically implanted onto a blood vessel. While continuous and instantaneous blood flow measurements are possible, measurement accuracy is dependent on vessel preparation during the implantation, and the surgery itself is a high risk procedure.

Non-invasive approaches have been developed to avoid the risks associated with invasive procedures; however, when information concerning patient hemodynamic variables such as central pressure, pulmonary artery pressure, capillary wedge pressure, and systemic arterial pressure is required, an invasive technique must be used. One noninvasive approach includes the use of a transthoracic impedance transducer which measures impedance changes in the thorax to calculate blood flow. The accuracy of this technique is reduced by patient movement which can affect the output. Doppler ultrasound methods are generally the most non-invasive means to measure blood flow, but are expensive and bulky, and may require some invasive measurements to completely assess the patient's hemodynamic status. In addition, the location of the ultrasound probes has to be exact and may interfere with other probes in the thoracic cavity.

Other attempts at determining the cardiac output in a relatively non-invasive manner have attempted to do so by taking integrals of the arterial pressure waveform over time, which can be approximately related to stroke volume and hence cardiac output. However, it must be stressed that stroke volume is a time-varying, non-linear function of arterial pressure, as well as other cardiovascular variables such as arterial resistance, arterial compliance, ventricular contractility and heart rate. Prior methods can be termed "pulse contour" methods and attempt to solve the non-linear arterial pressure function by replacing it with a simple, time-invariant, linear differential equation. The simplified differential equation, however, is only an approximation to the actual arterial function, and may not accurately represent the actual arterial pressure function. For example, it has been found that at lower pressures in young and healthy individuals, compliance is relatively linear. However, even at lower pressures, compliance is nonlinear in many older individuals. Also, at higher pressures in both young and old individuals, compliance can be extremely nonlinear thus resulting in inaccurate cardiac output measurement results with these methods.

Referring to FIG. 1 in which a pressure waveform 10 is shown, the events of the cardiac cycle as they relate to pressure waveforms in the arteries will now be described. The cardiac cycle can be divided into two periods, systole 12 and diastole 14, and these periods can be further subdivided. Systole 12 is the period of the cardiac cycle during which the heart contracts. Ventricular systole lasts about 0.3 seconds, while atrial systole lasts about 0.1 seconds. Diastole 14 is the period between two contractions of the heart, when the muscle of the heart relaxes and allows the chambers to fill with blood. Ventricular diastole lasts about 0.5 seconds in a normal heart rate of about 70 beats per minute. In the normal young adult the pressure peak at systole is about 120 mm.Hg, while the pressure at the nadir of the cycle, at diastole, is about 80 mm.Hg. The difference between these two pressures, 40 mm.Hg, is the pulse pressure. The FIG. also presents a dicrotic notch 16 in the pressure waveform 10.

In general, the shape of an arterial pressure waveform 10 is due to a variety of factors some of which are nonlinear and are related in a non-linear manner, and include different rates of transmission and distortion in the components of a pressure wave, interference with standing or reflected waves, differences in the elasticity and diameter of arteries, as well as the conversion of kinetic energy to static pressure.

For purposes of illustration only, the cardiac cycle can be simplified and approximated by an RC circuit, where the resistor R and capacitor C are in parallel with a time varying current supply E(t). The voltage drop across the resistor is $P_a-P_v$. This so called Windkessel model of the cardiac cycle, whose differential equation equating flow is represented by:

$$E(t) = C \frac{dP(t)}{dt} = \frac{1}{R} P(t)$$

where:

E(t)=flow into the Windkessel model during systole;
P(t)=differential pressure of the arteries compared to the veins $(P_a-P_v)$;
C=Windkessel arterial compliance; and
R=Windkessel peripheral resistance.

Solution of this differential equation is assumed to give a representation of the cardiac cycle. The initial conditions are determined by whether the cycle is in systole whereupon the current supply E(t) is assumed to be connected in parallel with the RC circuit, or whether the cycle is in diastole, whereupon it is assumed E(t) is removed from the rest of the circuit by opening a switch. This represents diastolic runoff into the peripheral circulation. The current stored in the capacitor is then discharged through the resistor, and the voltage P(t) (which corresponds to the arterial pressure in the heart) is given by:

$$P(t) = E_{DP} * \exp \frac{(t_{ED} - t)}{RC}$$

where:

$E_{DP}$=end diastolic pressure; and
$t_{ED}$=time at end of diastole.

However, despite the simple solution to this differential equation, the difficulty in the solution lies with determining the coefficients of peripheral resistance (R) and arterial compliance (C). Lacking these two values, it is impossible to directly integrate the pressure function contour over time to determine cardiac output. As a consequence, most researchers have chosen to use indirect methods of solving the Windkessel equations, in which the stroke volume is determined without explicit knowledge of R and C. Specific approaches include the methods of Hamilton and Remington (1947), Warner (1953) and (1968), Kouchoukos (1970), Bourgeois (1976), Guier (1974), Smith and Wesseling (1974), Brubakk (1980), and the Harley and Herd methods, all of which are known to those skilled in the art. Each of these techniques employs various ratios of integrals of the pressure waveform and a proportionality constant.

Potential problems and sources of error of these pulse contour methods of measuring cardiac output based on the Windkessel equations include:

(1) the relationship between changes in pressure and blood volume is assumed to be linear and constant, which may not be the case in clinical settings;

(2) the Windkessel equation is a linear differential equation with constant coefficients, while arterial pressure is a non-linear function;

(3) for all the above mentioned techniques, an independent measure of stroke volume or cardiac output is required for every patient tested in order to evaluate the proportionality constant. Also, due to the timevarying nature of the variables, repeat calibration is often required during monitoring;

(4) all of the above mentioned techniques require knowledge of a systolic time interval for the determination of the systolic pressure area or end systolic pressure. To calculate the systolic time interval, an accurate measurement of the arterial pulse transmission time is necessary, which is difficult to measure. Some techniques require measurement of the time of the dicrotic notch; however, it is often difficult to accurately determine that time. In addition, the systolic time interval depends on the heart rate and mean arterial pressure; and (5) most of the above mentioned techniques (excluding Guier's) assume that the diastolic drainage is equal to the arterial uptake. This relationship, however, may be significantly violated during conditions often seen in a real hospital setting, such as irregular heartbeats, aortic valve closure failures and other cardiac arrhythmias.

Hence, those concerned with determining cardiac output and other vascular system characteristics of a patient have recognized the need for an improved, relatively simple, less invasive, and accurate system for continuously determining and displaying data concerning such characteristics. Additionally, those concerned have also recognized the need for a system and method which is more accurate over a variety of patients. The present invention fulfills these needs and others.

SUMMARY OF THE INVENTION

Briefly, and in general terms, the present invention is related to a system and method for determining the value of a characteristic of the vascular system of a patient from the blood pressure existing in that vascular system. In one aspect of a system in accordance with the invention, a sensor senses the blood pressure in the vascular system and a digitizer converts the blood pressure signal into a digitized pressure signal. A memory contains a plurality of representative pressure waveforms, each representative pressure waveform comprising a set of values of selected features of a respective pressure signal having associated therewith a known value of the characteristic. The memory also stores the known characteristic value corresponding to each representative pressure waveform. A processor receives the digitized pressure signal, extracts at least one feature of the selected set of features from the digitized pressure signal and determines the value of each extracted feature, compares the value of each extracted feature from the digitized pressure signal to the value of each corresponding feature of representative pressure waveforms stored in the memory, based on the comparison, selects the representative pressure waveform most similar to the digitized pressure signal, and provides the characteristic value corresponding to the selected representative pressure waveform as the value of the characteristic of the vascular system of the patient.

In another aspect, the system monitors the blood pressure signals to determine the existence of a single beat frame of a heart. Features from the waveform residing in that single beat frame are extracted for processing as described above.

In further aspects, the sensor senses the blood pressure continuously and the digitizer continuously converts the pressure signal into a digitized pressure signal. The value of the determined vascular system characteristic is displayed, in one case visually, and in another is recorded such as by printing.

Additionally in another feature, the processor extracts all of the selected features from the digitized pressure signal and determines the value of each extracted feature for comparison to stored representative pressure waveforms.

In yet a further aspect, the representative pressure waveforms comprise classes of actual pressure signals generated by vascular systems having known values of the characteristic, the classes resulting from application of a pattern recognition method to the actual pressure signals. In one particular aspect, the Typical Shape Function pattern recognition method was applied to the actual pressure signals to result in the classes.

Features extracted from the pressure waveforms may include the pressure at the end of diastole, the systolic pressure, the pressure of the dicrotic notch, the time at the end of diastole, the time of systolic pressure, the time of the dicrotic notch, the period of the cardiac cycle, the rate of the cardiac cycle, and/or a mathematical feature selected from the group consisting of: the exponential decay time constant of the pressure signal; the derivative of the pressure signal at the systolic pressure; the coefficients of the Fourier Series of the pressure signal; the coefficients of the Fourier Contours of the pressure signal; the Fourier Transform of the pressure signal; the Beta-spline description of the pressure signal; the mean, the maximum, the minimum, the standard deviation, covariance or entropy of the pressure signal.

The system and method of the invention may be used to determine arterial resistance, arterial compliance, ventricular contractility, and cardiac output of the heart from the pressure signal as the characteristic of the patient's vascular system.

In one aspect of a method in accordance with the invention, the method includes the steps of sensing the blood pressure in the vascular system, converting the sensed blood pressure into a digitized pressure signal, storing a plurality of representative pressure waveforms, each representative pressure waveform comprising a set of values of selected features of a respective pressure signal having associated therewith a known value of the characteristic and storing the known characteristic value corresponding to each representative pressure waveform, extracting at least one feature of the selected set of features from the digitized pressure signal and determining the value of each extracted feature, comparing the value of each extracted feature from the digitized pressure signal to the value of each corresponding feature of representative pressure waveforms stored in the memory, based on the comparison, selecting the representative pressure waveform most similar to the digitized pressure signal, and providing the characteristic value corresponding to the selected representative pressure waveform as the value of the characteristic of the vascular system of the patient.

In another aspect of a method in accordance with the invention, a single beat frame of a heart is identified and the step of extraction is applied to the data in that beat frame. In a further aspect, the step of sensing comprises the step of continuously sensing the blood pressure and the step of converting comprises continuously converting the pressure signal into a digitized pressure signal.

The method may further comprise the step of displaying the characteristic value corresponding to the selected representative pressure waveform on a visual display and/or a recorder, such as a printer.

In other aspects, the step of extracting comprises the step of extracting all of the selected features from the digitized pressure signal and determining the value of each extracted feature. The step of storing representative pressure waveforms comprises the steps of sensing actual pressure signals generated by vascular systems having known values of the characteristic, applying a pattern recognition method to the actual pressure signals to result in a plurality of classes each with a corresponding value of the characteristic. In a further aspect, the step of applying a pattern recognition method comprises applying a Typical Shape Function pattern recognition method to the actual pressure signals to result in the classes.

Other features and advantages of the present invention will become apparent from the following detailed description, taken in conjunction with the accompanying drawings, which illustrate, by way of example, the principles of the invention.

DESCRIPTION OF THE PREFERRED EMBODIMENT

Figure 2:
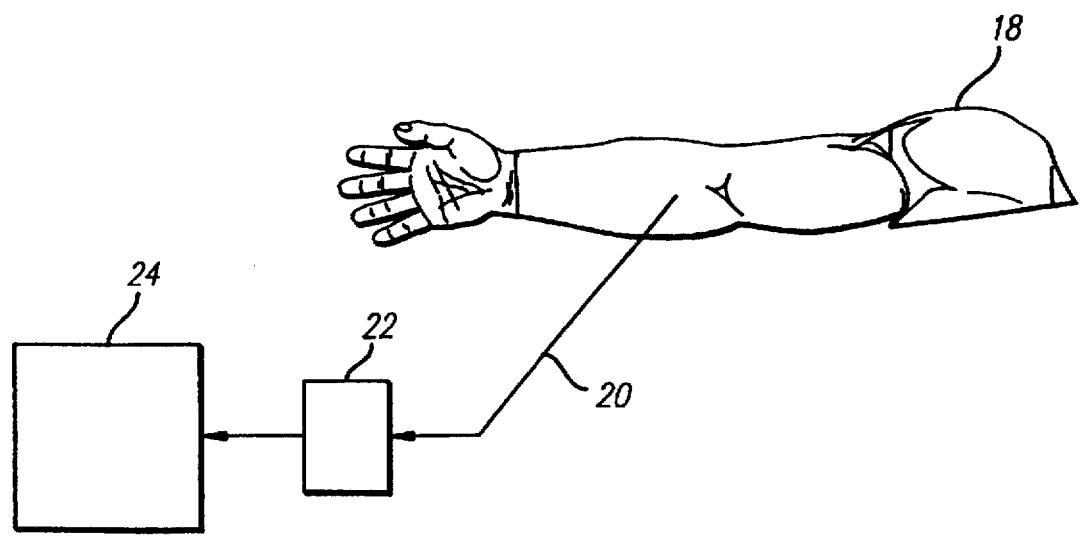
FIG. 2 is a block diagram of a system used to monitor the arterial pressure of a patient.

Referring now to the drawings with more particularity, wherein like reference numerals designate like or corresponding elements among the several views, there is shown in FIG. 2 an overview of a less invasive system incorporating principles of the invention which senses the blood pressure of a patient 18 and determines a characteristic of the patient's vascular system from the blood pressure waveform. The system includes a "fluid line" catheter 20 connecting the arterial pressure of the patient to a pressure sensor 22 and a processing system 24. The preferred embodiment has a fluid line catheter 20 disposed in the radial artery of the patient 18 and a pressure sensor 22 such as a strain beam type coupled to that fluid line 20 to provide pressure signals so that an accurate reading of aortic pressure can be obtained. Various such blood pressure measuring catheters exist. It is envisioned, however, that other pressure sensors could be employed, including pressure sensors that measure blood pressure in a non-invasive manner. These include, for example, Doppler ultrasound sensors, pressure sensitive means such as strain gauges or tonometers, or other pressure measuring means that can sense or compute arterial pressure.

Figure 3:
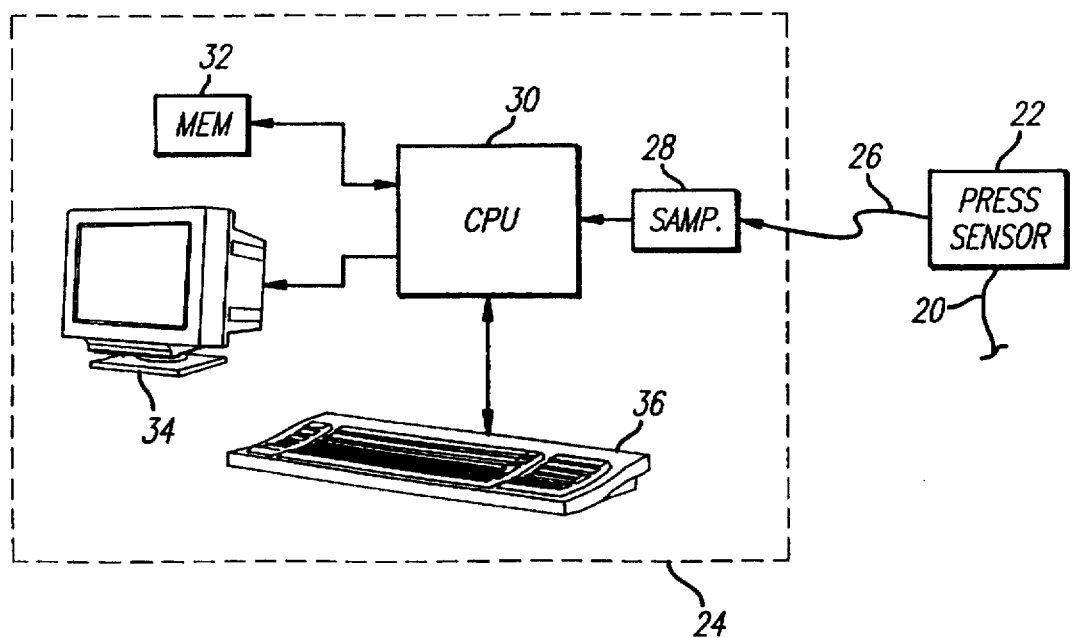
FIG. 3 is a schematic block diagram of a system for determining the value of a characteristic of the vascular system of a patient in accordance with principles of the invention including a processing system which receives a pressure signal, converts it to a digital signal, compares it to stored data, and provides a characteristic value based on the comparison.

Referring to FIG. 3, there is shown a schematic block diagram of the processing system 24 employing digital sampling of arterial pressures to ascertain cardiac output in accordance with one embodiment of the invention. The line 26 from the pressure sensor 22 continuously supplies analog pulse pressure data representing the instantaneous aortic pressure sensed. A sampling circuit 28 contains an analog-to-digital (A/D) converter and a sample-and-hold circuit to convert the analog data from the sensor 22 to digital form and supply the central processing unit (CPU) 30 with a continuous stream of digitally sampled pressure waveforms (DSW) representing arterial pressure. Thus, the CPU 30 can selectively read pressures from the sensor 22 in a sampled fashion to get a discrete, digital representation of the instantaneous pressures over a discrete set of times. At all times the actual arterial pressure from the sensor 22 has to be sampled repeatedly enough to keep errors due to improper sampling low. Thus, the Nyquist rate for sampling is a recommended guide for the frequency of sampling desired to convert the analog pressure waveform into an adequate digital representation. In practice, it has been found that a sampling rate of at least 25 Hz, and preferably 100 Hz results in adequate accuracy.

Figure 1:
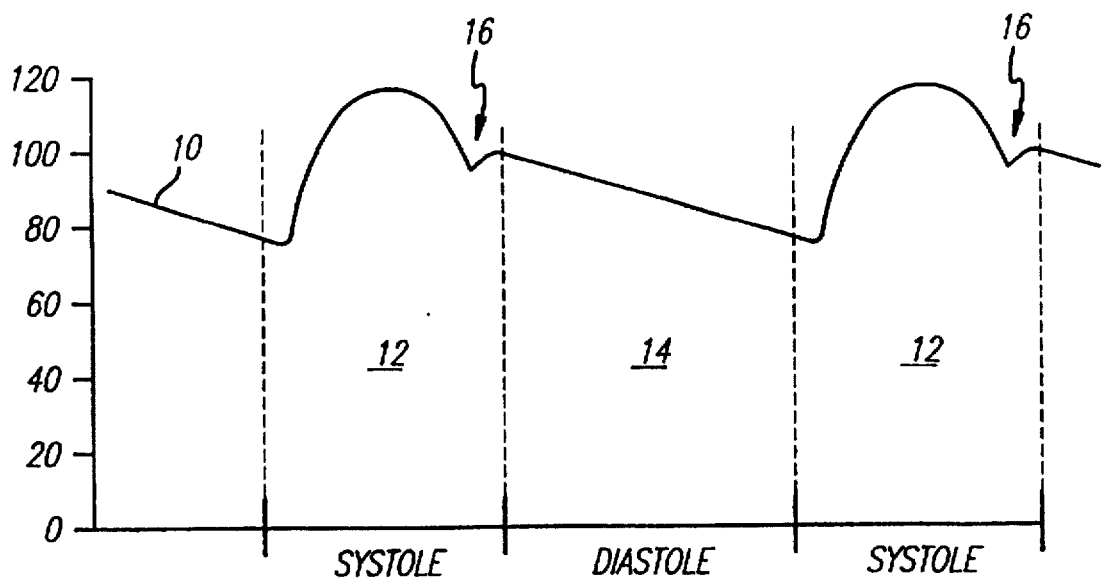
FIG. 1 is a graph of an arterial aortic pressure waveform having labels indicating systole, diastole, and the dicrotic notch.

The digitally sampled pressure waveform (DSW) is analyzed by the CPU 30 to obtain a set of data corresponding to a complete heart beat (a "beat frame"). In order to determine whether a complete heart beat has occurred, the sampled data representing a waveform for a given period is compared by the CPU 30 to a representative waveform such as that shown by FIG. 1 stored in memory 32, to determine whether or not the sampled waveform is of sufficient shape and geometry to constitute a complete beat frame. A template-matching procedure such as one involving a running-window correlator well known in the art of pattern recognition per se is preferred.

After identifying a set of data representing a complete beat frame, the CPU 30 proceeds to extract selected features of this beat frame waveform and compare those extracted features to corresponding features of waveforms stored in the processor's memory 32 which are representative of heart beat frames having known cardiac outputs. After identifying the stored waveform which is closest to the DSW beat frame, the cardiac output of that stored waveform is then displayed on a monitor 34. The keyboard 36 or other device may be used by an operator to communicate with the system 24.

In order to process a digitally sampled waveform in accordance with the principles of the invention for use in generating the stored database of RPW's and in determining the cardiac output from a DSW, it is important to ascertain an a priori set of features or parameters that are most likely to identify a human heartbeat. These features or parameters can range from every single X,Y pair to a sample of them, to abstract features of the waveform. Some of the most important a priori parameters for the aortic pressure waveform have been found to include: the pressure and time at the end of diastole, the time of the opening of the aortic valve; the pressure and time of peak (systolic) pressure; the pressure and time of the dicrotic notch; the heart rate or its period; the exponential decay time constant, which is defined as the time that it takes for the aortic pressure waveform to decay to $1/e^{th}$ of its peak value at diastole (where "e" is the base of the natural logarithm); and the derivative of the pressure waveform during systole.

In addition, there are select abstract features that can be calculated from the digitally sampled waveform after the waveform has been normalized that can help identify the waveform. These abstract features include the coefficients of the Fourier Series and the Fourier Contours. Other abstract features of the digitally sampled waveform may include such statistical parameters as the mean of the magnitude of points, the maximum and minimum values of the data points, the standard deviation, covariance and entropy of the points, the statistical moments of the data points, and other gradient methods. In addition the Beta-spline descriptions of the digitally sampled waveform for each heartbeat can be used as a parameter. The definitions of these statistical parameters and Beta-spline descriptions of complex curves are known in the art per se.

Figure 4:
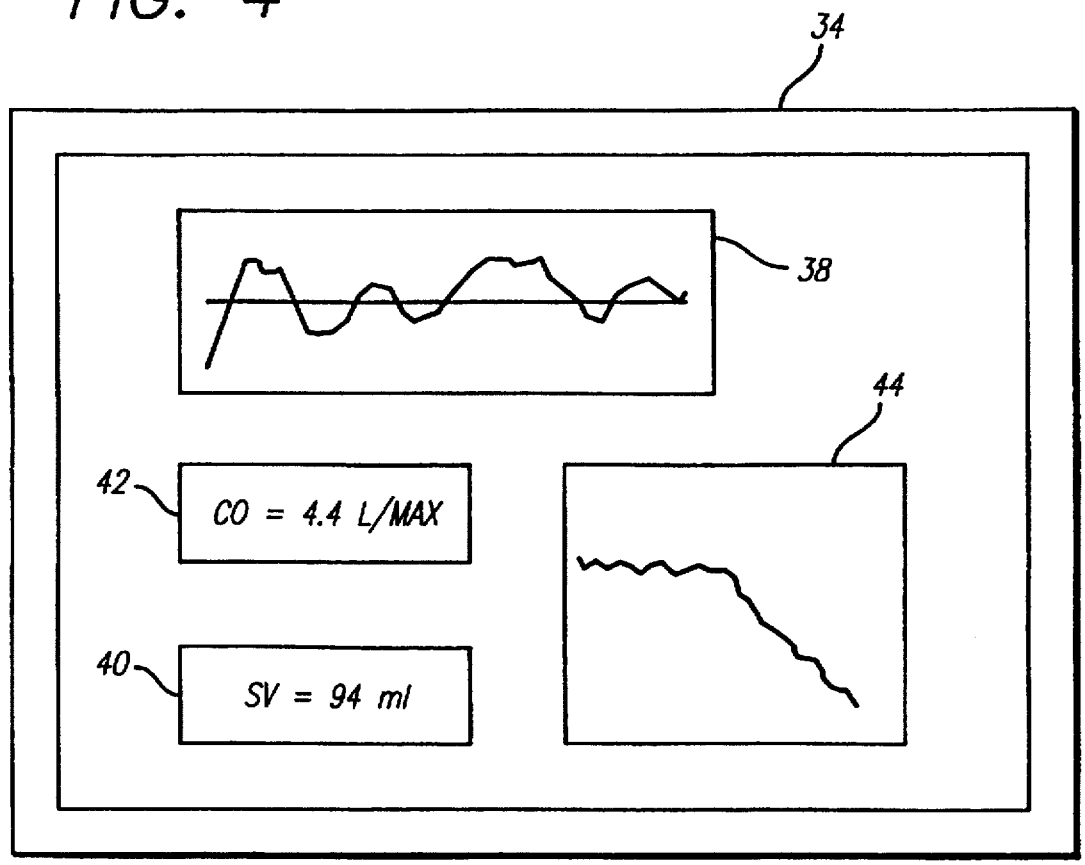
FIG. 4 is a display of cardiac output and other characteristics of a vascular system.

These identifying features are extracted from a DSW produced by a cardiovascular system having an unknown cardiac output and are compared to features stored in the processor's memory 32 here termed "stored representative pressure waveforms (RPW)" each of which was produced by a cardiovascular system which had a known cardiac output. The cardiac output value for each representative pressure waveform is also stored in memory 32. There may be thousands of stored RPW's. When a match is made between the DSW features and the features of an RPW, the CPU 30 selects that matching RPW and looks up the cardiac output associated with the selected RPW. The cardiac output of the selected RPW is then read from memory 32 and is assigned as the cardiac output for the DSW by the CPU 30. That cardiac output value is then provided to a display device such as a visual display monitor 34 and/or a recording device such as a strip chart recorder or a printer. A sample display 34 is presented in FIG. 4 where a pressure waveform is shown 38, a stroke volume number is given 40, and a digital display 42 of instantaneous or average cardiac output and an analog display 44 of cardiac output trend is provided.

Representative pressure waveforms (RPW's) are derived from actual patient pressure waveforms where the cardiac output is known. The pressure waveforms and corresponding cardiac outputs (CO) are collected from numerous healthy and ill patients spanning the range of possible arterial pressures and cardiac outputs. There may be many tens of thousands or hundreds of thousands of actual pressure waveforms taken of patients. To keep the size of the stored database of RPW's manageable so that searching and matching processes are not unduly delayed by having to search through many waveforms which are very similar, the "raw" pressure waveforms from patients having known cardiac outputs are subjected to a pattern recognition method to result in classes. The DSW of an unknown cardiac output is then "classified" by comparing its features to the stored classes (RPW's) to determine which class the DSW falls in. After making that determination, the cardiac output for that class is assigned to the DSW.

A pattern recognition methodology known in the art as "typical shape function" analysis (TSF) is the preferred method of generating the classes (RPW's). TSF analysis is mentioned in the work of Jalickee and Ropolewski, "An Objective Analysis Of The Boundary Layer Thermodynamic Structure During GATE", 107 *Monthly Weather Review* 68–76 (1979), and L. M. McMillin, Use Of Typical Shape Functions Of Radiance Vectors In Satellite Retrievals, *Advances In Remote Sensing Retrieval Methods*, published by IFAORS, A.Deepak, Editor, 1985.

The raw pressure waveforms, as represented by the selected features, from patients having known cardiac output are stored in a matrix A, called the shapes matrix, having M rows and N columns. Every row of the shapes matrix can be considered as describing a single raw pressure waveform and each column represents a single feature. The TSF analysis is performed on the shapes matrix, extracting the most distinguishable types of rows of the matrix. The first step in this analysis is to compute the L leading terms (a function of the number of classes to be determined) of the asymptotic singular value decomposition of A. This decomposition relates a series of orthogonal vectors, which are intrinsically defined by the shapes matrix, to the shapes matrix which when properly combined, reconstruct A in a special way. The characteristic feature of this expansion is that the terms of the expansion are optimal, in the sense of least squares, and ordered according to their importance to the successive approximation of A.

The shapes matrix is approximated by the L leading terms of the expansion. This approximation is then rotated in an optimal way and a new expansion is obtained. This new expansion is such that every row of the original shapes matrix A can be represented by one of the vectors in the expansion. This new set of vectors is defined as the typical shapes. This gives us the classifying criterion: rows of A corresponding to the same typical shape belong to the same class (RPW). Now new pressure waveforms can be classified by selecting the same features used to describe the RPWs, and comparing them (using some measure) with the typical shapes. For example, the difference between each DSW feature and RPW feature for all classes can be determined, squared, and all squared differences summed. The class having the lowest sum of squared differences would be selected and its cardiac output would be assigned as the cardiac output for the DSW.

The mathematical transformation involved in the TSF analysis will now be described. The following description is not intended to be exhaustive of the methodology entailed by the TSF analysis, but is intended to give an overview of the methodology, which is known to those skilled in the art, and described in the aforementioned work by Jalickee and Ropolewski, as well as the dissertation by L. Volfson, "Pattern Recognition And Classification And Its Application To Pre-processing Arterial Pressure Waveform Signals And Image Processing Problems," University of California, San Diego, 1990.

The first step in TSF analysis is to decompose the shapes matrix A, representing the digitally sampled pressure waveforms of known cardiac output, by a singular value decomposition (SVD) means into the form:

$$A = X \Lambda Y_T$$

where:

A is real M×N (M≧N) of rank L≦M;

X is a M×N column-orthogonal left singular vector matrix;

Y is a N×N orthogonal right singular vector matrix; and $\Lambda$ is the N×N diagonal matrix of the positive or zero singular values.

Matrix A components thus appear to be expanded into sums such as:

$$A_{ij} = \lambda_1 x_j^{(1)} y_i^{(1)} + \lambda_2 x_j^{(2)} y_i^{(2)} + \ldots + \lambda_L x_j^{(L)} y_i^{(L)}$$

where the singular values of $\Lambda$, $\lambda_1 \geq \lambda_2 \geq \ldots \geq \lambda_L > 0$ are all real, positive square roots of the positive eigenvalues of the M×M matrix $AA^T$ ($A^T$ is the transpose of the matrix A), or the N×N matrix $A^T A$, and the vectors x and y are the left and right singular vectors of A, which are orthogonal and normal.

To effect the decomposition of matrix A, a fast iterative technique known in the art as the Asymptotic Singular Decomposition (ASD) is used. Details of the ASD procedure are known in the art and can be seen, for example, in the aforementioned Volfson dissertation, pp 8 through 10.

Summing the L leading terms of the SVD of the matrix A yields an approximation of A in the form:

$$A_{i,j} = \sum_{k=1}^{L} \lambda_k x_j^{(k)} y_i^{(k)} = \sum_{k=1}^{L} a_j^{(k)} y_i^{(k)} \quad i=1, \ldots M; j=1, \ldots N$$

where M is the number of rows of the shapes matrix A and N is the number of columns (number of extracted parameters).

As we are interested in the rows of matrix A (individual pressure waveforms), the I-th row of the approximation can be viewed as a linear combination of vectors $a^{(k)}$ taken with corresponding coefficients $y_i^{(k)}$. Thus vectors $a^{(k)}$ can be viewed as some basic shapes which constitute the rows of A (i.e. every pressure waveform is a combination of some basic shapes).

The main objective of TSF is to obtain another expansion for the shapes matrix A:

$$A_{i,j} = \sum_{k=1}^{L} \hat{a}_j^{(k)} \hat{y}_i^{(k)}$$

while preserving the same approximation. This new expansion is such that every row of A has in its expansion one dominant coefficient, i.e., for every i there exists such number p that:

$$|\hat{y}_i^{(p)}| >> |\hat{y}_i^{(k)}|, k=1, \ldots L$$

This means that every row of the shapes matrix can be expressed by one shape function $\hat{a}^{(p)}$. This gives the classifying criterion: rows of matrix A (RPWs) corresponding to the same function $\hat{a}^{(p)}$ belong to the same class.

The problem is to find a relationship between the new vectors and the old vectors. In fact, there is a relationship, and it can be viewed as changing the basis of vectors $a_j^{(k)}$, $y_i^{(k)}$ by a rotation, though the new vectors $\hat{y}_i^{(k)}$ are not necessarily linearly independent. Thus, mathematically, we can relate the old and new vectors via rotation matrices $\alpha$ and $\beta$ as follows:

$$\hat{y}_i^{(m)} = \sum_{k=1}^{L} \alpha_{m,k} y_i^{(k)}$$

$$\hat{a}_j^{(n)} = \sum_{k=1}^{L} \beta_{n,k} a_j^{(k)}$$

It also is true that $\alpha^-=\beta$, and that matrix $\alpha$ is an L×L matrix, with L being the number of leading terms of the matrix A expansion.

This optimization problem of finding a relationship between the old and new vectors, through a rotation matrix $\alpha$ given the constraint that the vectors should remain normalized, can be recast as a minimization problem that can be restated in terms of Lagrange multipliers as:

$$\min_{\alpha_{k,k'}, k, k' = 1, \ldots L} \left( \sum_{\substack{m,n=1 \\ m \neq n}}^{M} \sum_{i=1}^{L} |\hat{y}_i^{(m)} \hat{y}_i^{(n)}|^2 + \sum_{m=1}^{K} \mu_m \left[ 1 - \sum_{i=1}^{M} \hat{y}_i^{(m)} \hat{y}_i^{(n)} \right] \right)$$

where μm are Lagrange multipliers.

This optimization problem can be solved readily on a computer using an iterative technique where one vector $\hat{y}^{(m)}$ is calculated while the rest of the vectors $\hat{y}^{(n)}$ are fixed (m≠n), which corresponds to varying only one row of the rotation matrix α instead of all the components of the matrix.

After simplifying the minimization problem and making suitable substitutions for $\hat{y}_i^{(m)}$ we get a minimum function that is quadratic. Differentiating this minimum function with respect to $\alpha_{m,k}$ with k=1, ..., L, we can find the local minimum of this minimum function by is solving the eigenvalue problem:

$$\sum_{k'=1}^{K} A_{k,k'}^{(m)} \alpha_{m,k'} = \mu_m \alpha_{m,k} \quad k = 1, \ldots K$$

and by definition:

$$A_{k,k'}^{(m)} = \sum_{\substack{n=1 \\ (n \neq m)}}^{K} \sum_{i=1}^{M} y_i^{(k)} \hat{y}_i^{(m)} \hat{y}_i^{(n)} y_i^{(k')}$$

The solution to the minimization function is the eigenvector corresponding to the smallest eigenvalue.

On a computer, this solution is found by going through two nested loops. The inner loop, which is iterated L times, consists of vectors $\hat{y}^{(m)}$ for m =1, ..., L. After each step of this loop the new values of the m-th row of rotation matrix α are computed. The outer loop consists of the whole set of vectors $\hat{y}^{(m)}$, and the rotation matrix α is updated each time this loop is passed through. The iteration through the outer loop is terminated whenever the difference between two consecutive matrices α is smaller than some predetermined convergence parameter.

When the rotation matrix α is calculated to the desired degree of accuracy, its inverse, matrix β is calculated, and the new basis of shape functions is:

$$\hat{a}_j^{(m)} = \sum_{k=1}^{L} \beta_{m,k} a_j^{(k)}$$

This new set of vectors $\hat{a}^{(k)}$ is called the typical shapes.

At this point, we have a set of typical shape vectors (RPW's). Now we can classify DSW's for any patient by computing the same set of features from that DSW and comparing them with these typical shapes. The closest typical shape (RPW) defines the class of the particular DSW and hence the cardiac output represented by the waveform.

Figure 5:
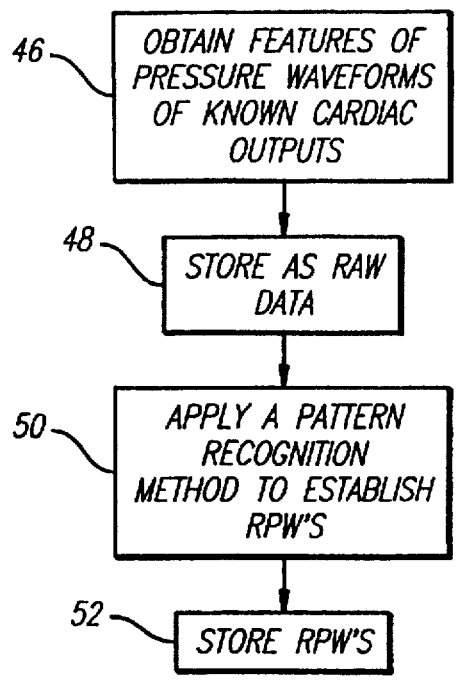
FIG. 5 is a flow chart of a method used to construct the stored database of representative pressure waveforms used by the processing system.

Referring now to FIG. 5 in more detail, an overview flow chart is presented in which representative pressure waveforms are generated. Pressure waveforms are obtained which are representative of known cardiac outputs. Features of those waveforms are extracted 46 and are stored as raw data 48. A pattern recognition methodology, such as typical shape function, is applied 50 to develop representative pressure waveforms. The RPW's are then stored 52 for later use in classifying pressure waveforms representative of unknown cardiac outputs.

Figure 6:
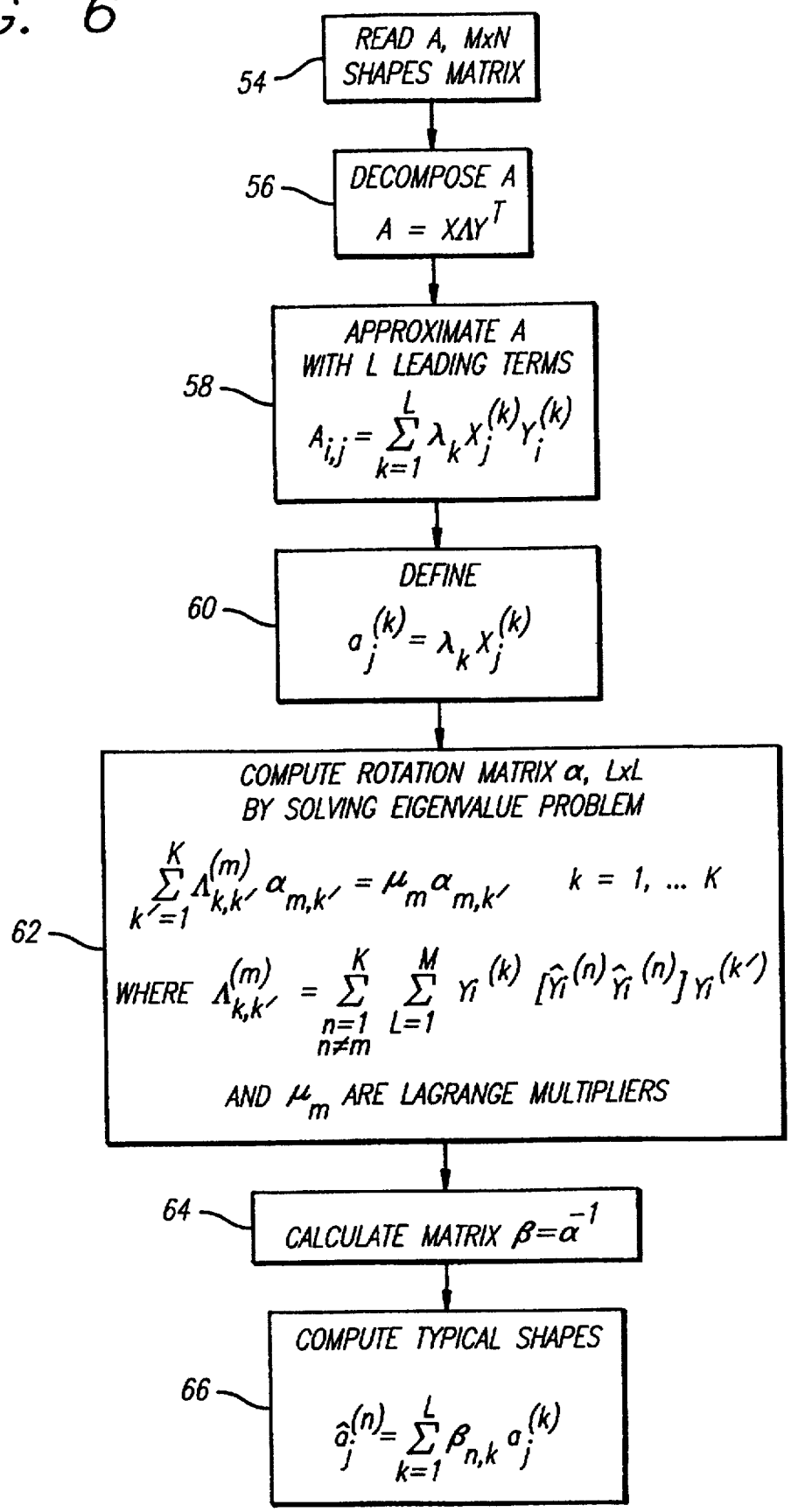
FIG. 6 is a flow chart of a pattern recognition method used to obtain the classes stored as the representative pressure waveforms in FIG. 5.

FIG. 6 presents a more detailed block diagram of the establishment of the RPW's through application of the typical shape function methodology. The extracted features of the pressure waveforms representative of known cardiac outputs are organized in a matrix as described above and that matrix is read 54, decomposed 56 and approximated with L leading terms 58. Terms are defined 60 and the rotation matrix α is computed 62. From the rotation matrix, the matrix β calculated 64 and the typical shapes are generated 66 (RPW's).

Figure 7:
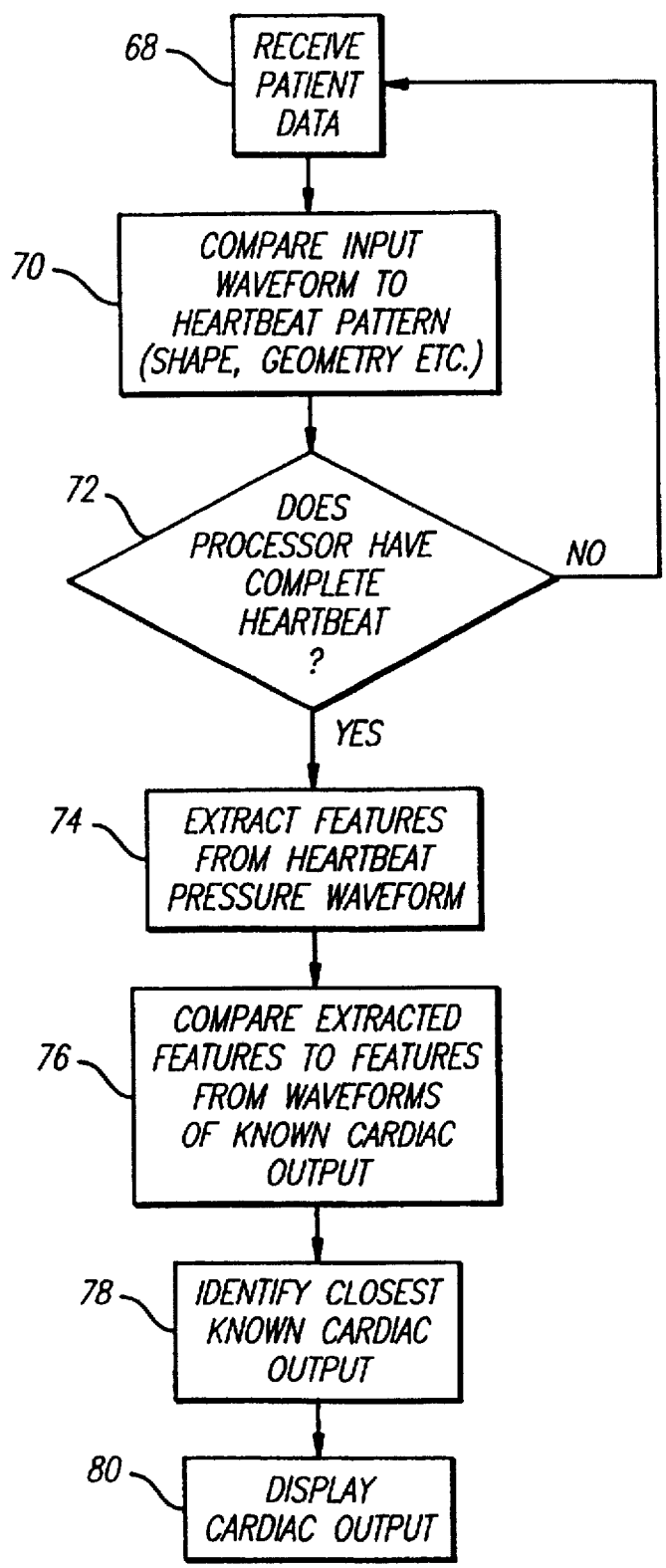
FIG. 7 is a flow chart of a method in accordance with the invention used to receive the pressure signal from a patient having an unknown cardiac output and determine the patient's cardiac output from that pressure signal.

Referring now to FIG. 7, an overview flow chart is presented concerning a method for determining cardiac output from a patient's pressure waveform. Data from the patient is received 68 and is compared 70 to a heart beat pattern to identify a complete beat frame The data is monitored to determine if a complete beat frame is present 72 and until the complete frame is present, additional patient data is received 68 and monitored 70. A running window correlator may be used to determine the existence of a complete beat frame.

When the complete frame is present, features are extracted 74 and are compared 76 to stored features (RPW's) representative of known cardiac outputs. The closes RPW is identified and selected 78 and the cardiac output of that selected RPW is displayed 80 as the cardiac output of the patient.

Figure 8:
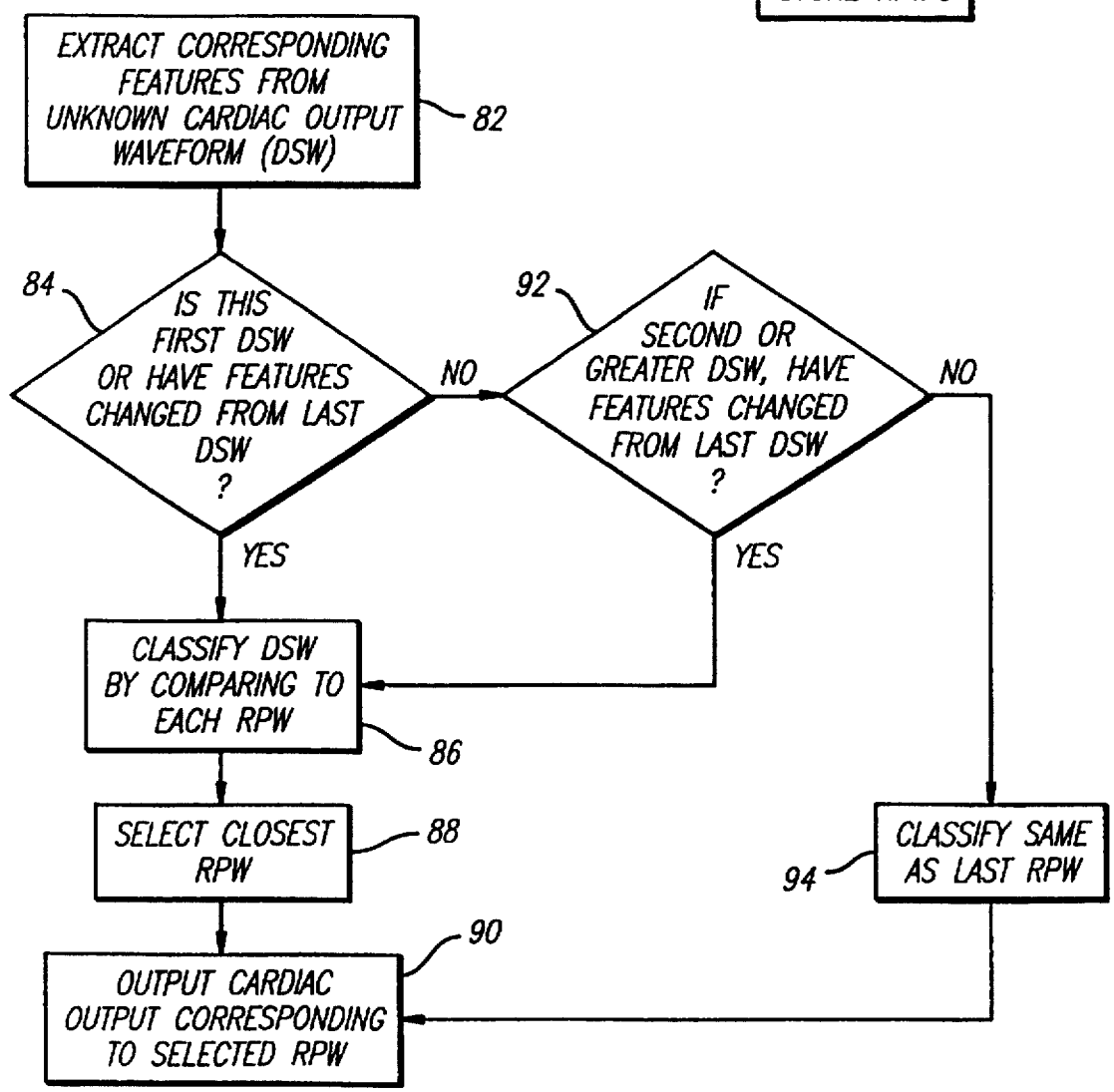
FIG. 8 is a more detailed flow chart of a method used to extract features from a pressure waveform, classify that set of features, and provide a cardiac output value based on that classification.

FIG. 8 presents a flow chart of a technique for selecting the RPW and its cardiac output as described above. The features are extracted 82 from the waveform representative of an unknown cardiac output and it is determined if this is the first digitally sampled waveform (DSW) or if it is not the first, if the features of this DSW have changed from the features of the last DSW 84. If this is the first DSW or if features have changed from the last DSW, the DSW is classified by comparing it to RPW's 86. Although in this embodiment the DSW is compared to all RPW's, other embodiments may include selective comparisons. In those embodiments, the DSW may be pre-grouped and compared only to certain RPW's. The closest RPW is selected 88 and the cardiac output associated with that selected RPW is output as the cardiac output of the DSW 90.

If this is the second or greater DSW and features have changed from the last DSW 92, the DSW is classified 86, an RPW selected 88 and a cardiac output provided 90 as described previously. However, if this is the second or greater DSW and features have not changed from the last DSW 92, this DSW is classified the same as the last DSW 94 and the same cardiac output of the last DSW is applied to this DSW 90.

While an average of cardiac output may be displayed, all heart beats are sampled in this embodiment. Therefore, in another embodiment, the instantaneous CO could be displayed.

Using the techniques of the present invention in actual animal models in which over 200,000 representative pressure waveforms were taken from individual cardiovascular system beats that covered a significant range of hemodynamic conditions, the mean error in calculated cardiac output when compared to ultrasonic flow probe techniques of measuring cardiac output was 2.8%, with a standard deviation of 9.8%. Six to eight thousand distinct classes were obtained.

In addition, it is possible, using the same method to associate arterial resistance, compliance, and ventricular contractility with a digitally sampled waveform. In these instances, the processor would store values relating arterial resistance and compliance with a representative pressure waveform (RPW), and when a match is made between a digitally sampled waveform and a representative pressure waveform, the values associated with the representative pressure waveform could be read from memory.

The present invention can be relatively non-invasive, and does not require calibration or collaboration using highly invasive measurements such as in the prior art. In this embodiment, the radial artery only was used. In addition, the present invention involves real time solutions to the non-linear relationship between arterial pressures and cardiac output, and does not rely on solving simplified equations to achieve a solution.

The present invention may have applications outside the measurement of cardiac output using pressure waveforms, to include interpretation of other waveforms, such as from electrocardiogram (ECG) as a coronary heart disease predictor or electroencephalography (EEG) for the depth of anesthesia.

It will be apparent from the foregoing that, while particular forms of the invention have been illustrated and described, various modifications can be made without departing from the spirit and scope of the invention. Accordingly, it is not intended that the invention be limited, except as by the appended claims.

I claim:

1. A system for determining the cardiac output of a cardiovascular system from the blood pressure developed by the cardiovascular system, comprising:
    a sensor which senses the blood pressure developed by the cardiovascular system and which provides a pressure signal representative of that blood pressure;
    a digitizer which receives the pressure signal from the sensor and converts the pressure signal into a digitized pressure signal;
    a memory having stored therein a plurality of representative pressure waveforms, each representative pressure waveform comprising a set of values of selected features of a respective pressure signal developed by a cardiovascular system having a known cardiac output, the memory also storing the known cardiac output value corresponding to each representative pressure waveform; and
    a processor which:
        receives the digitized pressure signal from the digitizer;
        extracts at least one feature of the selected set of features from the digitized pressure signal and determines the value of each extracted feature;
        compares the value of each extracted feature from the digitized pressure signal to the value of each corresponding feature of representative pressure waveforms stored in the memory;
        based on the comparison, selects the representative pressure waveform most similar to the digitized pressure signal; and
        provides the cardiac output value corresponding to the selected representative pressure waveform as the cardiac output of the cardiovascular system.

2. The system of claim 1 wherein the memory has stored therein representative pressure waveforms wherein each representative pressure waveform comprises a set of values of selected features derived from pressure signals monitored over a single beat frame of a heart.

3. The system of claim 1 wherein the sensor senses the blood pressure continuously and the digitizer continuously converts the pressure signal into a digitized pressure signal.

4. The system of claim 1 further comprising a display device which receives the cardiac output value from the processor and displays that value.

5. The system of claim 4 wherein the display device comprises a monitor which visually displays the cardiac output.

6. The system of claim 4 wherein the display device is a recorder which records the cardiac output.

7. The system of claim 1 wherein the processor further:
    extracts all of the features of the selected features from the digitized pressure signal and determines the value of each extracted feature; and
    compares the values of the extracted features of the digitized pressure signal to the values of the corresponding features of representative pressure waveforms; and
    selects the representative pressure waveform having feature values closest to the corresponding extracted feature values of the digitized pressure signal and provides the cardiac output value of the selected representative pressure waveform as the cardiac output of the cardiovascular system.

8. The system of claim 1 wherein the memory has stored therein representative pressure waveforms which comprise classes of actual pressure signals generated by cardiovascular systems having known cardiac output values, the classes resulting from application of a pattern recognition method to the actual pressure signals.

9. The system of claim 8 wherein the memory has stored therein representative pressure waveforms which comprise classes of actual pressure signals generated by cardiovascular systems having known cardiac output values, the classes resulting from application of a Typical Shape Function pattern recognition method to the actual pressure signals.

10. The system of claim 1 wherein at least one of the selected features is selected from the group consisting of: the pressure at the end of diastole; the systolic pressure; or the pressure of the dicrotic notch.

11. The system of claim 1 wherein at least one of the selected features is selected from the group consisting of: the time at the end of diastole; the time of systolic pressure; the time of the dicrotic notch; the period of the cardiac cycle; or the rate of the cardiac cycle.

12. The system of claim 1 wherein at least one of the selected features is a mathematical feature selected from the group consisting of: the exponential decay time constant of the pressure signal; the derivative of the pressure signal at the systolic pressure; the coefficients of the Fourier Series of the pressure signal; the coefficients of the Fourier Contours of the pressure signal; the Fourier Transform of the pressure signal; the Beta-spline description of the pressure signal; the mean, the median, the maximum, the minimum, the standard deviation, covariance or entropy of the pressure signal.

13. A method for determining the cardiac output of a cardiovascular system from the blood pressure developed by the cardiovascular system, comprising the steps of:
    sensing the blood pressure developed by the cardiovascular system and providing a pressure signal representative of that blood pressure;

converting the pressure signal representative of sensed blood pressure into a digitized pressure signal;

storing a plurality of representative pressure waveforms, each representative pressure waveform comprising a set of values of selected features of a respective pressure signal developed by a cardiovascular system having a known cardiac output, and storing the known cardiac output corresponding to each representative pressure waveform;

extracting at least one feature of the selected set of features from the digitized pressure signal and determining the value of each extracted feature;

comparing the value of each extracted feature from the digitized pressure signal to the value of each corresponding feature of representative pressure waveforms stored in the memory;

based on the comparison, selecting the representative pressure waveform most similar to the digitized pressure signal; and providing the cardiac output value corresponding to the selected representative pressure waveform as the cardiac output of the cardiovascular system.

14. The method of claim 13 wherein the step of extracting comprises the step of extracting at least one feature from the digitized pressure signal over a single beat frame of a heart.

15. The method of claim 13 wherein the step of sensing comprises the step of continuously sensing the blood pressure and the step of converting comprises continuously converting the pressure signal into a digitized pressure signal.

16. The method of claim 13 further comprising the step of displaying the cardiac output value corresponding to the selected representative pressure waveform.

17. The method of claim 16 wherein the step of displaying comprises the step of visually displaying the cardiac output value corresponding to the selected representative pressure waveform.

18. The method of claim 16 wherein the step of displaying comprises the step of recording the cardiac output value corresponding to the selected representative pressure waveform.

19. The method of claim 13 wherein:

the step of extracting comprises the step of extracting all of the selected features from the digitized pressure signal and determining the value of each extracted feature;

the step of comparing comprises comparing the values of the extracted selected features of the digitized pressure signal to the values of the corresponding features of representative pressure waveforms;

the step of selecting comprises selecting the representative pressure waveform having feature values closest to the corresponding extracted feature values of the digitized pressure signal;

the step of providing comprises providing the value of the cardiac output of the selected representative pressure waveform as the cardiac output value of the cardiovascular system.

20. The method of claim 13 wherein the step of storing representative pressure waveforms comprises the steps of:

sensing actual pressure signals generated by vascular systems having known cardiac outputs;

applying a pattern recognition method to the actual pressure signals to result in a plurality of classes each with a corresponding cardiac output value; and storing the classes and respective corresponding cardiac output values.

21. The method of claim 20 wherein the step of applying a pattern recognition method comprises applying a Typical Shape Function pattern recognition method to the actual pressure signals to result in the classes.

22. The method of claim 13 wherein the step of extracting comprises extracting at least one of the selected features from the group consisting of: the pressure at the end of diastole; the systolic pressure; or the pressure of the dicrotic notch.

23. The method of claim 13 wherein the step of extracting comprises extracting at least one of the selected features is selected from the group consisting of: the time at the end of diastole; the time of systolic pressure; the time of the dicrotic notch; the period of the cardiac cycle; or the rate of the cardiac cycle.

24. The method of claim 13 wherein the step of extracting comprises extracting at least one of the selected features is a mathematical feature selected from the group consisting of: the exponential decay time constant of the pressure signal; the derivative of the pressure signal at the systolic pressure; the coefficients of the Fourier Series of the pressure signal; the coefficients of the Fourier Contours of the pressure signal; the Fourier Transform of the pressure signal; the Beta-spline description of the pressure signal; the mean, the median, the maximum, the minimum, the standard deviation, covariance or entropy of the pressure signal.

25. A system for determining the cardiac output of a cardiovascular system from the blood pressure developed by the cardiovascular system, comprising:

a sensor which continuously senses the blood pressure developed by the cardiovascular system and which provides a pressure signal representative of that blood pressure;

a digitizer which receives the pressure signal from the sensor and continuously converts the pressure signal into a digitized pressure signal;

a memory having stored therein a plurality of representative pressure waveforms, each representative pressure waveform comprising a set of values of selected features of a respective pressure signal developed by a cardiovascular system over a single beat frame, the representative pressure waveforms comprising classes of actual pressure signals generated by cardiovascular systems having known cardiac output values, the classes resulting from application of a pattern recognition method to the actual pressure signals, the memory also storing the known cardiac output value corresponding to each representative pressure waveform;

a processor which:

receives the digitized pressure signal from the digitizer;

extracts all the features of the selected set of features from the digitized pressure signal and determines the value of each extracted feature;

compares the values of the extracted features from the digitized pressure signal to the values of the corresponding features of representative pressure waveforms stored in the memory;

based on the comparison, selects the representative pressure waveform having feature values closest to the corresponding extracted feature values of the digitized pressure signal; and provides the cardiac output value corresponding to the selected representative pressure waveform as the cardiac output of the cardiovascular system.

26. The system of claim 25 wherein the memory has stored therein representative pressure waveforms which comprise classes of actual pressure signals generated by cardiovascular systems having known cardiac output values, the classes resulting from application of a Typical Shape Function pattern recognition method to the actual pressure signals.

27. A method for determining the cardiac output of a cardiovascular system from the blood pressure developed by the cardiovascular system, comprising the steps of:

continuously sensing the blood pressure developed by the cardiovascular system and providing a pressure signal representative of that blood pressure;

continuously converting the pressure signal representative of sensed blood pressure into a digitized pressure signal;

storing a plurality of representative pressure waveforms, each representative pressure waveform comprising a set of values of selected features of a respective pressure signal developed by a cardiovascular system over a single beat frame, the representative pressure waveforms comprising classes of actual pressure signals generated by cardiovascular systems having known cardiac output values, the classes resulting from application of a pattern recognition method to the actual pressure signals, and storing the known cardiac output value corresponding to each representative pressure waveform;

extracting all the features of the selected set of features from the digitized pressure signal and determining the value of each extracted feature;

comparing the values of the extracted features from the digitized pressure signal to the values of the corresponding features of representative pressure waveforms stored in the memory;

based on the comparison, selecting the representative pressure waveform having feature values closest to the corresponding extracted feature values of the digitized pressure signal; and providing the cardiac output value corresponding to the selected representative pressure waveform as the cardiac output of the cardiovascular system.

28. The method of claim 27 wherein the step of storing comprises storing classes resulting from the application of a Typical Shape Function pattern recognition method.

* * * * *

UNITED STATES PATENT AND TRADEMARK OFFICE
CERTIFICATE OF CORRECTION

PATENT NO. : 5,797,395
DATED : Aug. 25, 1998
INVENTOR(S) : James F. Martin

It is certified that error appears in the above-identified patent and that said Letters Patent is hereby corrected as shown below:

Column 10, line 3, change "$A=X^\wedge Y_T$", to read --$A=X^\wedge Y^T$--.

Signed and Sealed this

Twelfth Day of January, 1999

*Attest:*

*Attesting Officer*   *Acting Commissioner of Patents and Trademarks*